United States Patent [19]

Hofen et al.

[11] 4,341,709
[45] Jul. 27, 1982

[54] PREPARATION OF ε-CAPROLACTONE

[75] Inventors: Willi Hofen, Rodenbach; Herbert Klenk; Gerd Schreyer, both of Hanau; Otto Weiberg, Bruchkoebel; Helmut Waldmann, Leverkusen; Hermann Seifert, Cologne; Karl-Hermann Reissinger, Leverkusen; Wolfgang Swodenk, Odenthal-Gloebusch, all of Fed. Rep. of Germany

[73] Assignee: Bayer Aktiengesellschaft, Leverkusen, Fed. Rep. of Germany

[21] Appl. No.: 150,260

[22] Filed: May 15, 1980

[30] Foreign Application Priority Data

May 19, 1979 [DE] Fed. Rep. of Germany ....... 2920436

[51] Int. Cl.³ ........................................... C07D 313/02
[52] U.S. Cl. .................................................... 549/272
[58] Field of Search ..................... 260/343; 203/71, 73

[56] References Cited

U.S. PATENT DOCUMENTS 3,056,802 10/1962 Phillips et al. ...................... 260/343
3,064,008 11/1962 Phillips et al. ...................... 260/343
3,517,033 6/1970 Weiberg .............................. 260/343

OTHER PUBLICATIONS

Starcher et al., J.A.C.S., pp. 4079–4081, 1958.

Primary Examiner—Jane T. Fan
Attorney, Agent, or Firm—Sprung, Horn, Kramer & Woods

[57] ABSTRACT

A process for the preparation of ε-caprolactone comprising:
(a) reacting cyclohexanone with a solution of perpropionic acid in an organic solvent at a molar ratio of cyclohexanone:perpropionic acid of about 1.1–5:1 at a temperature of about 10° to 80° C. to form a reaction mixture consisting essentially of ε-caprolactone, propionic acid and organic solvent,
(b) distilling the reaction mixture from (a) in a first distillation unit to obtain a distillate comprising the organic solvent and a distillation residue,
(c) introducing the distillation residue from (b) at a point into a second distillation unit to obtain a distillate comprising propionic acid and unreacted cyclohexanone, removing from the second distillation unit, separately from one another and at a point below the point of introduction into the second distillation unit, ε-caprolactone and any high-boiling constituents, and,
(d) distilling in a third distillation unit the distillate from (c) to obtain a distillate consisting essentially of propionic acid and a distillation residue comprising a mixture of propionic acid and cyclohexanone.

20 Claims, 3 Drawing Figures

PREPARATION OF ε-CAPROLACTONE

The present invention relates to a continuous process for the industrial preparation of ε-caprolactone. In particular, the present invention relates to a process for the preparation of ε-caprolactone by reacting organic solutions of perpropionic acid with cyclohexanone.

ε-Caprolactone and its alkyl derivatives are important industrial products which, by polymerization or copolymerization, for example with epoxides, can be processed to high-molecular products which can be used both in the field of synthetic resins and in the field of foams. In addition, ε-caprolactone itself is a suitable starting material for ε-caprolactam, which is important in the field of synthetic fibers.

In accordance with the great industrial importance of this product, in the past there have been numerous attempts to discover simple and economically favorable processes for the preparation of ε-caprolactone which enable this compound to be prepared on an industrial scale without the formation of coupled products and by-products which pollute the environment.

The principal difficulties faced in successfully carrying out the oxidative conversion of a cyclic ketone into a lactone, by the so-called Baeyer-Villinger reaction (equation 1)

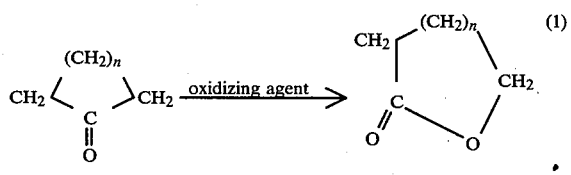

are to be found in the formation of by-products, which takes place to a considerable extent. By-products which are formed, for example, in the preparation of ε-caprolactone are, above all, polyesters of the lactone, polymeric peroxides, ω-hydroxy- and ω-acyloxycaproic acid and products which stem from the further oxidation of the ε-caprolactone, such as, for example, adipic acid (compare Houben-Weyl, Methoden der Organischen Chemie (Methods of Organic Chemistry), volume 6/2, 4th edition, 1963, pages 708–709 and page 777). However, not only the amount of by-products formed during the reaction, that is to say simultaneously with the ε-caprolactone, but also the extent to which additional amounts of undesired products, in particular polymers, are obtained on separation of the reaction mixtures is decisive for the industrial use of a particular oxidizing agent.

Attempts have therefore been made to discover oxidizing agents or solutions of oxidizing agents which permit essentially selective conversion of the cyclohexanone into ε-caprolactone. Attempts have also been made to use oxygen directly for the preparation of ε-caprolactone.

According to the process of German Auslegeschrift No. 1,289,840, cyclohexanol is treated with oxygen, cyclohexanone being used as the solvent. This process, which proceeds via the intermediate stage of cyclohexanol peroxide, gives only a low yield of ε-caprolactone since adipic acid, 6-hydroxycaproic acid and ester-like condensation products are also formed.

A process in which a hydroperoxide formed from a hydrocarbon and $O_2$ is used as the oxidizing agent has been disclosed in German Auslegeschrift No. 2,049,409. The reaction of the hydroperoxide with the cyclic ketone takes place using Friedel-Crafts catalysts. The use of such catalysts unavoidably gives rise to a high proportion of polymers, since, as is known, polymerization of ε-lactones can be initiated by these catalysts. In addition, the alcohol corresponding to the hydroperoxide used is obtained as a by-product in this process and cannot be recycled directly.

A further process in which oxygen or an $O_2$-containing gas is used for the formation of ε-caprolactone is to be found in German Auslegeschrift No. 1,443,188. According to this process, the oxidation is carried out in the presence of an aldehyde and using catalytic amounts of metal compounds. This process, like other processes based on these raw materials, has the disadvantage of production of by-products since the aldehyde employed is simultaneously converted into the corresponding carboxylic acid. Thus, for the preparation of ε-caprolactone based on these raw materials, not only must an aldehyde be made available, but a suitable use must also be found for the carboxylic acid product. In addition, the catalysts used in the process of German Auslegeschrift No. 1,443,188 not only make the working up of the reaction mixture containing ε-caprolactone difficult, but during the reaction also promote further oxidation of the ε-caprolactone already formed, to give adipic acid and other low-molecular compounds.

The process of German Auslegeschrift No. 1,643,750 avoids the use of catalysts by employing isobutyraldehyde as an oxidation auxiliary. However, the yields of 83% which can be achieved are in this case also inadequate for an industrial procedure. This process also has the fundamental problem of production of by-products resulting from the isobutyric acid obtained.

Besides oxygen, $H_2O_2$ has also been used as an oxidizing agent for the preparation of ε-caprolactone. A large number of inorganic substances have been used to activate the hydrogen peroxide, such as, for example, anhydrous hydrofluoric acid (Chemical Abstracts, volume 47 (1953), page 8,012) or selenic acid (Tetrahedron Letters, volume 13, (1959) page 1). These processes can yield only small amounts of monomeric ε-caprolactone.

A process for the simultaneous preparation of ε-caprolactone and 6-formyloxy-caproic acid is described in German Auslegeschrift No. 1,216,283. $H_2O_2$ is likewise used as the oxidizing agent in this process, but is partly converted into performic acid before the reaction with the cyclohexanone is carried out. In addition to the necessity of converting the 6-formyloxycaproic acid into ε-caprolactone in a subsequent process, the use of formic acid is also a disadvantage because of the corrosion problems associated therewith.

A process of this type in which by-products, such as ε-hydroxy- or ε-acyloxy-caproic acid and polymeric esters, obtained in the preparation of ε-caprolactone are worked up to give ε-caprolactone has been proposed in German Auslegeschrift No. 1,643,145. In this process, the by-products mentioned are heated to temperatures of 150°–350° C. with compounds containing boron.

A further process for the conversion of the polymeric esters of ε-caprolactone can be found in German Offenlegungsschrift No. 1,693,028. That the latter two processes are the subject of patents shows very clearly that the formation of by-products is the predominant problem in the preparation of ε-caprolactone.

U.S. Pat. No. 2,904,584 also describes attempts to oxidize cycloalkanones with peracetic acid in the presence of a cation exchange resin by gradually introducing the cycloalkanone into a mixture of the peracid and the cation exchanger which is kept at 70° to 80° C. The peracetic acid is prepared beforehand by reacting aqueous hydrogen peroxide with acetic acid. This procedure gives only a mixture of 6-acetoxycaproic acid, 6-hydroxycaproic acid, adipic acid and only small amounts of ε-caprolactone.

German Auslegeschrift No. 1,258,858 proposes using aqueous solutions of aliphatic percarboxylic acids for the preparation of ε-caprolactone.

The use of an approximately 60% by weight aqueous peracetic acid is said to be particularly advantageous for this purpose. The yields which can be achieved in the case of ε-caprolactone are 80–90%, which signifies a certain improvement compared with other processes. The amount of energy consumed in the production of the aqueous peracetic acid solution unavoidably required as an oxidizing agent for this process is high, since a mixture of $H_2O_2$, water, acetic acid and peracetic acid which has been brought to equilibrium with the aid of an acid catalyst is subjected to distillation and not only the peracetic acid but the water later contained in the aqueous solution must also be distilled (in this context, compare German Auslegeschrift No. 2,262,970, column 2, lines 9–15). In addition, the value of applying the process of German Auslegeschrift No. 1,258,858 on an industrial scale is severely limited by the problems which arise in choosing suitable materials for the equipment for such peracetic acid distillation processes and by the expensive safety measures. Moreover, the working up of a reaction mixture which, in addition to ε-caprolactone, also contains water and in which, furthermore, free carboxylic acid, such as, for example, acetic acid, is still present is extremely difficult and wasteful because of the particularly pronounced tendency of the lactone to polymerize under these conditions.

Since the carboxylic acid is to be recycled, it is necessary to separate the water from the carboxylic acid. This separation is expensive since the water must again be distilled.

The disadvantages described also remain in the case of the process of German Auslegeschrift No. 1,693,027. In this process, vapor mixtures containing peracetic acid and water are likewise used for the preparation of ε-caprolactone, that is to say an aqueous peracetic acid solution must first be distilled.

According to the Journal of the American Chemical Society, 80, 4079–82 (1958), attempts have furthermore been made to by-pass the difficulties arising when aqueous percarboxylic acid solutions are used for the preparation of ε-caprolactone from cyclohexanone by using organic solutions of percarboxylic acids, such as, for example, peracetic acid in acetone. However, this measure is only marginally successful, since when peracetic acid in acetone is used, very long reaction times of six and more hours are required to achieve yields of 85% in the case of ε-caprolactone. In addition, the acetic acid which forms from the peracetic acid must rapidly be separated off from the reaction mixture or from the ε-caprolactone if losses in yield by polymerization of the lactone are to be avoided.

It is thus proposed to use another solvent, such as, for example, ethylbenzene, which is capable of forming an azeotrope with acetic acid (loc. cit. 80, 4,080 (1958)). Using an auxiliary of this type means an additional expense.

According to German Auslegeschrift No. 1,086,686, besides peracetic acid, highly explosive acetaldehyde monoperacetate is also used as an oxidizing agent for converting cyclohexanone into the corresponding lactone.

Peracetic acid and acetaldehyde monoperacetate are each prepared by oxidation of acetaldehyde with oxygen. However, as is known, this method of converting aldehydes into percarboxylic acids by oxidation in an organic solvent has considerable disadvantages. On the one hand, highly explosive intermediate products are formed when the process is carried out (compare German Auslegeschrift No. 2,262,970), and this necessitates expensive safety devices when the process is carried out industrially. A further serious disadvantage is that when the oxidation has been carried out, for example the oxidation of cyclohexanone to ε-caprolactone, the particular carboxylic acids corresponding to the aldehydes are obtained as by-products which, in this case, cannot be re-used in the stage for the production of the solution of the percarboxylic acid (German Auslegeschrift No. 1,258,858, column 1, lines 23–31, and German Auslegeschrift No. 1,443,188, column 2, lines 7–16).

Moreover, it must be taken into consideration that the percarboxylic acid solutions obtained by the aldehyde oxidation process contain impurities which have arisen through the oxidative degradation of the aldehyde proceeding simultaneously with the preparation and which, because of their acid properties, are capable of already initiating, in the reaction mixture, the undesired polymerization of the lactone, leading to losses.

German Offenlegungsschrift No. 2,038,455 proposes a further process for the preparation of ε-caprolactone. This is an expensive, multi-stage process. An aqueous solution of $H_2O_2$ is first prepared by reacting cyclohexanol with molecular oxygen, subsequently hydrolyzing the cyclohexanol peroxide formed and extracting the $H_2O_2$ now present using water. Thereafter, the aqueous hydrogen peroxide is introduced into a phosphorus-containing solvent and the water is distilled off, after which a carboxylic acid and an acid catalyst are added to the organic solution of the $H_2O_2$. After adding an entraining agent, this agent is distilled off together with the water of the reaction from the peracetic acid formation reaction and the percarboxylic acid. The peracid obtained is now reacted with cyclohexanone. As can be seen from Example 1 of German Offenlegungsschrift No. 2,038,455, only a 70% yield of ε-caprolactone is obtained. The expenditure on equipment and energy required in carrying out such a process is very high, as can readily be deduced from the number of process steps.

Summarizing, on the basis of the literature on processes for the preparation of lactones representing the state of the art, it can be established that all the known processes, including the processes in which percarboxylic acids are used for the oxidation of cyclohexanones, are unable to present a satisfactory solution to the problems posed by industrial requirements and the question of profitability.

In contrast, it has now been found that ε-caprolactone can be prepared in a simple, technically and economically advantageous manner by reacting cyclohexanone with a percarboxylic acid when (a) a solution of perpropionic acid in an organic solvent is reacted with cyclohexanone in a molar ratio of cyclohexanone: perpropionic acid of about 1.1–5:1 at temperatures of about 10°–80° C., (b) the resulting reaction mixture essentially consisting of ε-caprolactone, cyclohexanone, propionic acid and organic solvent is passed to a first distillation unit where the organic solvent for the perpropionic acid is recovered as the distillate, (c) the bottom product from the first distillation unit is introduced into a second distillation unit where the propionic acid and cyclohexanone which has not been reacted in stage (a) are obtained as the top product and ε-caprolactone and any high-boiling constituents are removed, separately from one another, below the inlet from this second distillation unit and (d) the distillate, consisting of propionic acid and cyclohexanone, from the second distillation unit is transferred to a third distillation unit where a mixture consisting of propionic acid and cyclohexanone is obtained and propionic acid is recovered as the distillate.

Possible solvents for the perpropionic acid are all the organic solvents which are inert towards this percarboxylic acid.

Examples of solvents which have proved suitable are aromatic hydrocarbons which contain 6 to 10 carbon atoms, aliphatic or cycloaliphatic hydrocarbons, in each case containing up to 12 carbon atoms, chlorinated hydrocarbons which contain 1 to 10 carbon atoms and 1 to 4 chlorine atoms, esters of carboxylic acids containing 1 to 5 C atoms with straight-chain or branched alcohols having 1 to 8 C atoms in the molecule, and ethers which contain 2 to 10 C atoms. Examples of solvents which may be mentioned are: benzene, toluene, xylene, n-pentane, isooctane, cyclohexane, methylene chloride, chloroform, 1,2-dichloroethane, 1,2-dichloropropane, methyl acetate, ethyl acetate, n-propyl acetate, isopropyl acetate, n-butyl acetate, isoamyl acetate, methyl propionate, ethyl propionate, propyl propionate and butyl propionate, and chlorobenzene and ether. However, it is also possible to use mixtures of the solvents mentioned as the solvent for the perpropionic acid, in which case solvents which have similar boiling points are advantageously chosen as components of the mixture. A compound which has a boiling point at least 15° C. below the boiling point of propionic acid is advantageously used as the organic solvent for the perpropionic acid. Chlorinated hydrocarbons, such as methylene chloride, dichloroethane, 1,2-dichloropropane, trichloroethylene or tetrachloroethylene, or aromatic hydrocarbons, such as benzene, or ethers, such as diisopropyl ether, and esters, such as propyl acetate or propionate, or mixtures of these solvents are preferably used. Benzene, 1,2-dichloropropane and tetrachloroethylene are very particularly preferred solvents for the process according to the invention.

The concentration of the perpropionic acid in the organic solution used for the reaction with cyclohexanone can vary within wide limits. Concentrations of about 3 to 60% by weight are in general suitable. Solutions which contain about 5 to 50% by weight of perpropionic acid are preferably used, and those which contain about 5 to 30% by weight of perpropionic acid are very particularly preferred.

Organic solutions of perpropionic acid which are suitable for the process according to the invention can also contain free propionic acid in addition to the perpropionic acid. The amount of propionic acid which can be present in addition to the perpropionic acid is not significant for the process according to the invention. It can be greater or smaller than the amount of perpropionic acid in the solution. However, solutions in which the amount of propionic acid is less than that of perpropionic acid are in general reacted with the cyclohexanone. The propionic acid content of the perpropionic acid solution is, for example, about 1 to 50% by weight, preferably about 5 to 40% by weight and especially about 5 to 20% by weight.

In some cases, it can be advantageous to add a stabilizer to the organic perpropionic acid solution, which is substantially anhydrous and free from hydrogen peroxide. Stabilizers which can be used are carboxylic acids or polycarboxylic acids containing nitrogen or hydroxyl groups, and also phosphorus compounds, such as, for example, the sodium salts of polyphosphoric acids partially esterified with long-chain alcohols (compare D. Swern "Organic Peroxides" volume 1, page 350, 1st paragraph; Wiley-Interscience 1970). However, in many cases it is not necessary to stabilize the perpropionic acid solutions since substantial decomposition of the perpropionic acid, which has an adverse effect on the process, does not occur at the temperatures at which the process according to the invention is carried out.

The organic solution of perpropionic acid is obtained in an industrially advantageous manner, for example according to the process of German Patent Specification No. 2,262,970, by a procedure in which a reaction mixture obtained by reacting hydrogen peroxide, water and an acid catalyst with propionic acid is extracted with the inert organic solvent and, if appropriate, the extract, which essentially contains the perpropionic acid, is then dried.

The organic solutions of perpropionic acid used for the process according to the invention in general contain not more than about 5% by weight of water. Solutions of perpropionic acids which contain less than about 3% by weight of water are preferably suitable. Solutions of perpropionic acid in an inert organic solvent which contain less than about 1% by weight of water are particularly preferably used. Solutions which contain not more than about 0.5% by weight of water are very particularly preferred.

The content of free hydrogen peroxide in the organic solutions of perpropionic acid which are suitable for the process according to the invention is in general not more than about 2% by weight. Solutions which contain less than about 1% by weight of $H_2O_2$ are preferably employed. Organic solutions of perpropionic acid which contain less than about 0.25% by weight of hydrogen peroxide are very particularly preferred.

Organic solutions of perpropionic acid which are suitable for the process according to the invention in general still contain small amounts of acid catalyst if they are prepared under acid catalysis. The content of free strong acid, such as, for example, methanesulphonic acid, trifluoromethanesulphonic acid, perchloric acid, sulphuric acid, sulphonic acids of benzene or of naphthalene or trifluoroacetic acid, is in general less than about 1% by weight. Solutions with a strong acid content of less than about 0.1% by weight are particularly suitable. Organic solutions of perpropionic acid which contain less than about 100 ppm of strong acid are very particularly suitable.

The reaction of the organic solution of perpropionic acid with excess cyclohexanone according to process step (a) is carried out at temperatures from about 10° to 80° C., preferably at about 20° to 60° C.

The molar ratio of cyclohexanone to perpropionic acid is preferably about 1.1 to 5:1. It is especially advantageous to use about 1.5 to 2.5 mols of cyclohexanone per mol of perpropionic acid employed, for carrying out the process according to the invention.

The pressure is not decisive for the reaction. In principle, the reaction can be carried out under increased pressures or also under reduced pressure. The reactants can also partly be present in gaseous form.

The mixture can be cooled with a suitable medium in order to remove the heat of reaction. In order to adjust the reaction temperature exactly to the desired value, the pressure in the reaction vessel is chosen, for example, such that the reaction mixture just boils. The reaction is preferably carried out at pressures of about 0.8–1.3 bars.

The reaction can be carried out in the equipment customary for reactions of this type, such as stirred tanks, tube reactors or loop reactors. If the reaction is carried out continuously, a device which acts as a cascade of at least two ideally mixed tanks is in general used. It is particularly advantageous to use a reaction system which acts as a cascade of about 4 to 50, preferably about 5 to 20, ideally mixed tanks.

Besides following a procedure under isothermal conditions, that is to say maintaining a uniform temperature in the entire reaction mixture, it is also possible to carry out the reaction under conditions of a so-called temperature gradient, the temperature in general increasing as the reaction progresses. However, the reaction can also be carried out such that the temperature decreases as the reaction progresses.

The equipment for carrying out the reaction can be made from materials such as glass, enamel or alloyed high-grade steel.

Examples of suitable materials are those which, in addition to iron, essentially also contain chromium and nickel, such as, for example, a material with the DIN designation of 1.4571, which contains, in addition to iron, 17.5% by weight of chromium, 11.5% by weight of nickel, 2.25% by weight of molybdenum and up to 2% by weight of manganese, up to 1% by weight of silicon, up to 0.1% by weight of carbon and small amounts of titanium; or a material with the DIN designation of 1.4577 which contains, in addition to iron, 25% by weight of chromium, 25% by weight of nickel, 2.25% by weight of molybdenum and up to 2% by weight of manganese, up to 1% by weight of silicon, up to 0.06% by weight of carbon and small amounts of titanium.

The reaction time depends on the temperature, on the concentration of perpropionic acid and of cyclohexanone and on the nature of the solvent in which the perpropionic acid is used. The reaction conditions are as a rule chosen such that the perpropionic acid has reacted to the extent of over 99% after about 20 to 150 minutes, preferably after about 30 to 120 minutes.

The reaction mixture containing the ε-caprolactone is worked up according to process stages (b), (c) and (d) using several distillation steps.

Known tray columns or packed columns can be used industrially for carrying out this sequence of three distillation steps. Columns equipped with packings or baffles of wire gauze or glass fiber fabric are likewise suitable. A packing of a ceramic material can also be successfully used. It is furthermore possible to use a combination of tray columns and packed columns, for example such that the stripping section of a column is packed with Pall rings of high-grade steel, while bubble trays are used in the rectifying section of the same column.

Each of the three distillation columns used according to the invention is provided with an evaporator unit and a condensation system. Known constructions can be used for the evaporator, such as falling film evaporators, circulatory evaporators or climbing film evaporators, as well as thin film evaporators, or simple vortex tubes. Circulatory evaporators are in general particularly suitable for the process according to the invention. Combinations of a circulatory evaporator or falling film evaporator and a thin film evaporator are advantageously used for carrying out stage (c) of the process. The dimensions of these apparatuses are advantageously chosen so that the residence times of the particular bottom products in the column bottoms and in the evaporator units of the columns are less than about 15 minutes.

The entire distillation tower as well as the baffles and the evaporation and condensation devices can be made from any of the materials customarily used in chemical engineering, such as, for example, stainless high-grade steels which, in addition to iron, also essentially contain chromium and nickel as the alloying constituent.

The number of theoretical plates which a distillation column used in the process according to the invention generally possesses can vary within wide limits. About 3 to 50 theoretical plates are in general sufficient. The separation effort required in the column used in process step (b) essentially depends on the properties of the compound used as the solvent for the perpropionic acid.

The invention will be further described with reference to the accompanying drawing, wherein.

Figure 1:
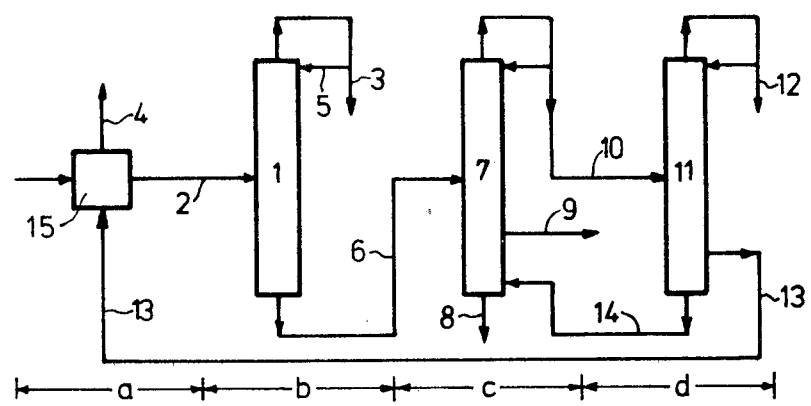
FIG. 1 is a flow sheet of a process in accordance with the present invention.

Referring now more particularly to FIG. 1, the reaction mixture from reactor 15 of stage (a) which contains, in addition to the organic solvent and propionic acid, about 5–30% by weight of ε-caprolactone and about 5–20% by weight of cyclohexanone is fed via line (2) to the first distillation unit (1) of stage (b), if appropriate after separating off small amounts of gaseous constituents. The organic solvent for the perpropionic acid is obtained as the top product in this first column. This solvent is recycled via line (3) to the production of the organic solution of perpropionic acid. The operating conditions in the first column are chosen such that the organic solvent obtained as the distillate contains less than 3% by weight, and particularly preferably less than 1% by weight, of propionic acid. The content of organic solvent in the mixture passing via (2) into the first column can vary within wide limits and is of no significance for the process according to the invention. The concentration of organic solvent in stream (2) is essentially determined by the content of perpropionic acid in the solution passed via (4) to reaction stage (a).

In general, a reaction mixture in which the weight ratio of propionic acid to cyclohexanone is 0.5–4:1, preferably 1–3:1, is passed to the first distillation column (1). It is especially preferable to choose a ratio of 1.5–2.5:1.

The distillation column used for process step (b) in general has a total of 2–50 theoretical plates. There are preferably 1–30 theoretical plates in the stripping section and 1–20 in the rectifying section.

The first column (1) can be operated under normal pressure or under slightly reduced pressure. However, it is also possible to operate the column under slightly increased pressure. The preferred pressure range is between 0.1 and 1.5 bars. It is especially advantageous to operate the column at 0.1–1.0 bar. The temperature range at which the first distillation unit is operated depends, of course, on the organic solvent used for the perpropionic acid; the temperature for the distillation can accordingly be varied within wide limits.

The reflux ratio, that is to say the ratio of the amount of organic solvent in stream (5) to the amount in stream (3), can be varied within wide limits.

This reflux ratio depends not only on the physical properties of the particular compound which has been chosen as the organic solvent for the perpropionic acid, but also on the number of plates in the first column. In general, a reflux ratio of 0.5–5:1 is sufficient for all the solvents in question. The reflux ratio chosen is preferably in the range from 0.5 to 2:1.

The organic solvent obtained as the product stream (3) can also contain, in addition to small amounts of propionic acid, very small amounts of water which may separate out as a light or heavy phase, depending on the density of the solvent. Since the amount of water is very low, in general no phase separation at all takes place. Any water which may be obtained as an aqueous phase in the top product of column (1) can be discarded or passed, at a suitable point, to the process stage for the production of the perpropionic acid solution.

According to process step (c), the bottom product from the distillation column (1), which essentially contains the ε-caprolactone, the propionic acid and the cyclohexanone employed in excess relative to perpropionic acid in stage (a), is now passed via line (6) to a second distillation unit (7) where propionic acid and cyclohexanone are obtained together as the top product, while ε-caprolactone is removed from column (7) at a point 1 to 15, preferably 3 to 10, theoretical plates above the bottom. Any higher-boiling constituents which may have been introduced into column (7) in small amounts with the product stream (6) or which may have been formed in this column, such as adipic acid and poly-caprolactone, are discharged via (8) as the bottom product. However, compared with known processes, this proportion of higher-boiling constituents is extremely low in the process according to the invention. It must furthermore be emphasized that no compounds of a peroxidic nature at all can be detected either in stream (6) or in the outflow (8) or in the product take-off (9). This is very advantageous from a safety point of view.

The inlet of stream (6) into this second distillation unit (7) is 1 to 20, preferably 2 to 15, theoretical plates above the point at which the ε-caprolactone is obtained in the lateral take-off (9). There are in general 3–20 theoretical plates in the column section above the inlet into column (7). This section of the column is advantageously designed such that it comprises 5–10 theoretical plates.

The pressure chosen in column (7) is 5–500 mbars. However, the column can also be operated under higher pressures, which of course results in higher top and bottom temperatures. It has proved particularly advantageous to choose a pressure, measured at the top of the column, in the range from 5 to 300 mbars. It is especially favorable to operate column (7) under a pressure which produces a temperature of 110°–140° C. at the point where the ε-caprolactone is removed in the side stream (9), taking into consideration the pressure losses resulting from the baffles in the column.

The reflux ratio with which an adequate separation of the mixture of propionic acid and cyclohexanone from the ε-caprolactone is achieved in column (7) with the given number of theoretical plates can be kept very small. In general, the reflux ratio is 0.5–5:1, and frequently is 0.5–3:1. It is particularly advantageous to operate the column at a reflux ratio of 0.5–1.5:1.

The composition of the mixture to be separated in column (7) can vary within wide limits. For example, the product stream (6) contains 10–40% by weight of ε-caprolactone, 35–55% by weight of propionic acid and 15–35% by weight of cyclohexanone. However, the concentrations of these three compounds are usually in the ranges from 20 to 35% by weight, 40 to 50% by weight and 20 to 30% by weight, respectively.

The ε-caprolactone removed via (9) as a side stream from column (7) has a purity of over 98% by weight and is already suitable for most application purposes. Propionic acid and cyclohexanone are virtually the only impurities contained in product stream (9). The ε-caprolactone removed via (9) has, for example, the following composition: 98–99% by weight of ε-caprolactone, 0.2–0.8% by weight of cyclohexanone and 0.3–0.7% by weight of propionic acid.

The ε-caprolactone removed from column (7) via (9) can optionally also be subjected to a still more intensive purification, for example by distillation, if this should be advisable for the particular intended use of the product.

As already mentioned, a mixture of propionic acid and cyclohexanone which can contain, without adverse effect, small amounts of ε-caprolactone is obtained as the top product of distillation unit (7). In general, the distillation conditions in column (7) are chosen such that the distillate contains less than 1% by weight, preferably less than 0.5% by weight, of ε-caprolactone. The weight ratio of propionic acid to cyclohexanone in the top product of column (7) is particularly preferably 1.5–2.5:1. For example, a mixture which, in addition to 65% by weight of propionic acid, contains 34.9% by weight of cyclohexanone and 0.1% by weight of ε-caprolactone is obtained.

According to the invention, the top product of column (7) is now passed via line (10) to process step (d), which is carried out in distillation unit (11). In process step (d), propionic acid is obtained, from product stream (10), as the distillate of column (11) and is recycled via (12) to the preparation of the organic solution of perpropionic acid. At the same time, a mixture of propionic acid and cyclohexanone is removed from (11) at a point between the inlet of stream (10) into column (11) and the bottom outlet (14). This mixture, which has a boiling point higher than that of propionic acid, is advantageously recycled via (13) to process stage (a), that is to say to the reaction of cyclohexanone with the organic solution of perpropionic acid.

This recycling of a mixture consisting of propionic acid and cyclohexanone represents a particular embodiment of the process according to the invention which proves to be of great advantage not only for carrying out process step (a) but also for the subsequent distillation steps (b), (c) and (d).

Under certain conditions, propionic acid and cyclohexanone form an azeotrope, that is to say a mixture with a constant boiling point. This azeotrope of propionic acid and cyclohexanone is described here for the first time. It has a boiling point of 92.2° C., for example, at a pressure of 133 mbars and has the following composition: 27.1% by weight of propionic acid and 72.9% by weight of cyclohexanone. The azeotrope, or a mixture of propionic acid and cyclohexanone close to the azeotropic point, is in general taken off from column (11) as stream (13) 1-10 theoretical plates above the bottom of the column.

However, it is also possible to remove the azeotrope or a mixture containing propionic acid and cyclohexanone from (11) as the bottom product. The product stream (13) is, however, preferably taken off at a point 1-5 theoretical plates above the bottom of column (11), and very particularly preferably at a point 1-3 theoretical plates above the bottom.

In general, the operating conditions of column (11), in particular the pressure and other parameters of the process according to the invention, are chosen such that the mixture consisting of propionic acid and cyclohexanone contains 0.5-50, preferably 15-40, % by weight of propionic acid. However, it is also possible for a mixture which contains more than 50% by weight or less than 15% by weight of propionic acid to be removed via (13) and recycled to stage (a), but it is advantageous for the composition of the product stream (13) to be close to the composition of the azeotrope. The concentration of propionic acid chosen in (13) is thus preferably in the range from 20 to 45% by weight, and very particularly preferably in the range from 25 to 35% by weight. The azeotropic composition, which is, for example, 27% by weight of propionic acid at a pressure of 133 mbars, can, of course, also be established exactly in stream (13). However, experience in continuous operation of the column (11) shows that, for trouble-free operation of the column, it is more favorable to choose a concentration of propionic acid in (13) slightly above that corresponding to the azeotropic composition, for example 33% by weight of propionic acid.

The small amount of bottom product obtained in column (11) is passed via (14) to column (7), where it is introduced at a point above that at which the ε-caprolactone is taken off in a side stream (stream (9)). The product stream (14) essentially contains propionic acid and cyclohexanone. Small amounts of ε-caprolactone and 2-cyclohexylidenecyclohexanone can also be present.

Propionic acid which contains less than 2% by weight of cyclohexanone, preferably less than 1% by weight and very particularly preferably not more than 0.5% by weight of cyclohexanone, is obtained as the top product (12) of distillation unit (11). The propionic acid taken off via (12) can contain small amounts of water. However, the content of $H_2O$ in (12) is in general not more than 0.2% by weight.

Column (11) is in general operated under pressures between 0.1 and 1.5 bars. The distillation in (11) is preferably carried out in the pressure range from 0.05 to 1.0 bar, and very particularly preferably in the range from 0.05 to 0.5 bar. The pressure in column (11) is advantageously chosen such that a temperature between 80° C. and 120° C. is established in the area where stream (13) is taken off.

The reflux ratio at which column (11) is operated can vary within wide limits, but reflux ratios of 3-15:1 are in general suitable to achieve less than 2% by weight of cyclohexanone in stream (12).

The reflux ratio chosen is preferably 5-10:1. The amounts of reflux into the column which thus result are then sufficient to keep the cyclohexanone content in (12) to values below 0.5% by weight if column (11) has a total of 50-70 theoretical plates, and the inlet of product stream (10) is then advantageously at a point 20-30 theoretical plates below the top of the column.

ε-Caprolactone can be prepared in yields of over 96%, relative to perpropionic acid employed, and at least 95%, relative to cyclohexanone employed, by the process according to the invention. These figures illustrate the advantages of the process according to the invention compared with all the previous processes. Furthermore, the ε-caprolactone prepared according to the invention has a high purity.

Figure 2:
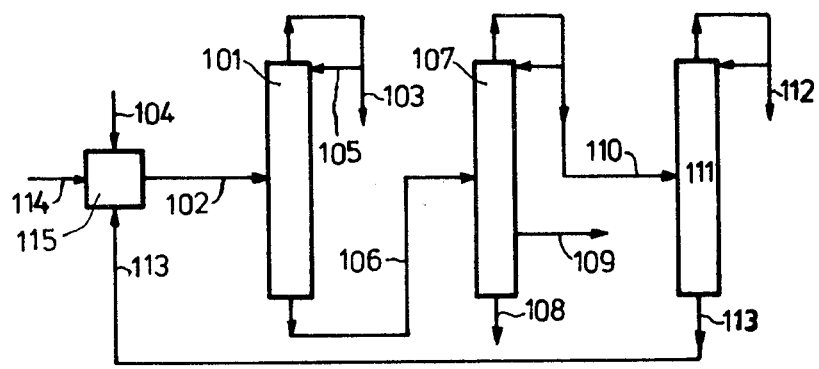
FIG. 2 is a flow sheet of another process in accordance with the invention.
Figure 3:
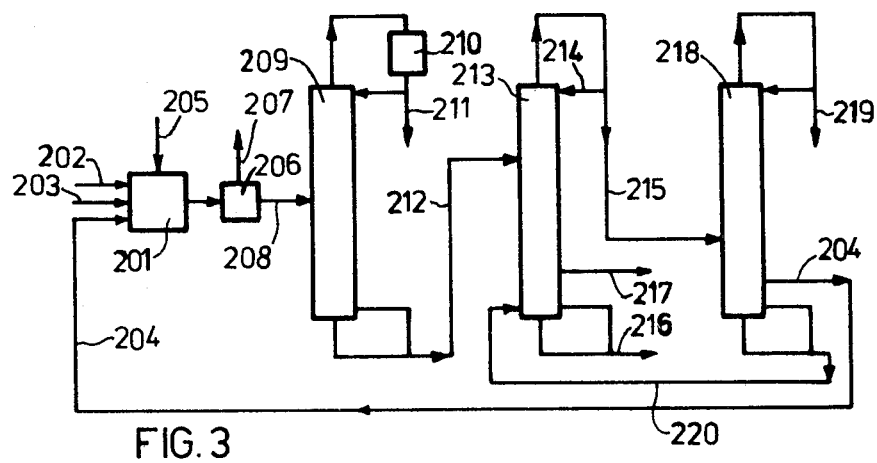
FIG. 3 is a flow sheet of still another process in accordance with the invention.

The embodiment of FIGS. 2 and 3 will now be described in Examples 1 and 2 with reference to actual operating conditions:

EXAMPLE 1 (FIG. 2)

Per hour, 16.58 kg (168.9 mols) of fresh cyclohexanone (114) and the sump outflow (113), which consists of 16.4 kg (167.1 mols) of cyclohexanone and 8.33 kg (112.5 mols) of propionic acid, are fed into one end of an approximately 175 l tube reactor provided with a double-wall jacket and made of material according to the DIN designation of 1.4571. At the same time, 76.644 kg per hour of a solution of perpropionic acid in benzene is fed at (104) continuously into the reactor (115) through the same opening. Precise analysis of this solution shows that 9.74 kg (131.5 mols) of propionic acid, 15.21 kg (168.9 mols) of perpropionic acid, 0.068 kg (2.0 mols) of hydrogen peroxide, 0.056 kg (3.1 mols) of water and 51.57 kg (660.2 mols) of benzene are fed in per hour. The temperature in the reaction tube is adjusted to about 50° C. by an external water circulation in the double-wall jacket. Only traces of perpropionic acid can still be detected at the end of the reaction tube.

The reacted mixture is now passed to a distillation unit (110) which consists of a packed column with an overall height of 5 m and a diameter of 0.2 m and with a packing of metal Pall rings. This stream (102) is introduced about 6 theoretical plates below the top of the column.

An overhead pressure at 0.43 bar is established in this column by means of a vacuum pump. The column is heated by a circulatory evaporator.

The ascending vapors are condensed completely at the top of the column and the liquid phase is divided into streams (103) and (105). 46.5 kg per hour are passed to the column as the reflux via stream (105), and 51.66 kg per hour are taken off as the distillate removal via stream (103), that is to say a reflux ratio of reflux: take-off =0.9 is established. Analysis of stream (103) shows that it consists of benzene to the extent of 99.8% and of water to the extent of 0.2%.

The remainder of stream (102) is removed from the bottom of the column as stream (106) and passed to distillation unit (107). Distillation unit (107) consists of a packed column which has an overall height of 7 m and a diameter of 0.3 m and is provided with a packing of metal Pall rings.

The inlet of stream (106) into column (107) is about 8 theoretical plates below the top of the column. In turn, there is an opening in the column about 8 theoretical plates below the inlet point, for the removal of a vaporous side stream. The bottom of the column is about 5 theoretical plates below this lateral take-off.

The column is heated by a thin film evaporator. An overhead pressure of 33 mbars is established in column (107) by means of a vacuum system. At the top of the column, the ascending vapors are passed through a dephlegmator which is adjusted, by water-cooling, such that a reflux ratio of 0.8 is obtained. The vapors rising through the dephlegmator are condensed completely in a further condenser and passed continuously, as stream (110), to distillation unit (111).

At the same time, ε-caprolactone is removed as a vapor in side stream (109). A thermometer located in this stream shows a vapour temperature of 135° C. The caprolactone vapour is condensed and weighed. 18.80 kg (164.7 mols) of ε-caprolactone are thus obtained per hour.

0.51 kg per hour of higher-boiling compounds which are not vaporized and discharged from the process via (108) pass through the thin film evaporator of column (107). The distillate of column (107), that is to say stream (110), is passed to a further distillation unit (111). This distillation unit consists of a packed column which has an overall height of 12 m and a diameter of 0.3 m, and metal Pall rings as the packing. An overhead pressure of 135 mbars is established in the column by means of a vacuum pump. The column is heated by a falling film evaporator.

The ascending vapors are condensed completely at the top of the column and some of the condensate is introduced into the column as the reflux. A reflux ratio of 6:1 is established. 22.25 kg per hour of liquid phase (112) are removed as the distillate take-off. Analysis by gas chromatography shows that this product consists of propionic acid to the extent of 99.95% and contains only traces of cyclohexanone and water.

Stream (113) is continuously removed from the bottom of this column and passed to the reaction system. Analysis of this stream shows that 16.4 kg (167.1 mols) of cyclohexanone per hour and 8.33 kg (112.5 mols) of propionic acid per hour are passed to the reaction system.

From the amount of caprolactone of 18.80 kg/hour contained in stream (109), a yield of 97.5%, relative to perpropionic acid in (104), and also of 97.5%, relative to cyclohexanone in (114), is calculated.

EXAMPLE 2 (FIG. 3)

The reaction between the solution of perpropionic acid in 1,2-dichloropropane and the cyclohexanone is carried out continuously in a five-stage reactor cascade (201). Each reactor has a volume of about 0.5 l and is provided with a stirrer. The first three reactors are operated at a temperature of 45° C., while the two subsequent reactors are each kept at 55° C. Downstream from the reactor cascade is a delay tube with a capacity of about 1.8 l. The temperature in this delay tube is kept at about 57°-58° C.

In continuous operation, 1,910 ml of a 16.5% strength by weight solution of perpropionic acid in 1,2-dichloropropane (stream 202) and, via line (203), 348 g of cyclohexanone with a purity of over 99.5% by weight are passed per hour into the reaction system described, via the first reactor. The solution of perpropionic acid contains 11.2% by weight of propionic acid, 0.2% by weight of hydrogen peroxide and about 0.1% by weight of water. The sulphuric acid content is less than 100 ppm. In addition to the perpropionic acid and the cyclohexanone (348 g), 508 g per hour of a mixture which, in addition to 33.27% by weight of propionic acid, contains 66.54% by weight of cyclohexanone and 0.19% by weight of ε-caprolactone are fed into (201) via line (204). The molar ratio of cyclohexanone to perpropionic acid fed in is thus 2:1. The reaction system (201) is operated at a pressure of 1.1 bars. Small amounts of nitrogen (10 l/hour) are introduced into the first reactor via line (205). The perpropionic acid conversion after the delay tube is determined as 99.8%. After passing through the delay tube, the reaction mixture is let down in tank (206), where, in addition to the nitrogen, small amounts of oxygen and $CO_2$ are also liberated. The stream of off-gas is removed via line (207).

The reaction mixture obtained after (206) in an amount of about 2.76 kg per hour contains, in addition to the 1,2-dichloropropane, 14.0% by weight of ε-caprolactone, 23.25% by weight of propionic acid, the excess cyclohexanone and 0.13% by weight of water, as well as about 0.5–0.55% by weight of high-boiling constituents. The reaction mixture is passed via line (208) to column (209), where the 1,2-dichloropropane is recovered as the top product. Column (209) has a diameter of 50 mm and 10 bubble trays in the stripping section and 15 bubble trays in the rectifying section. It is provided with a circulatory evaporator as the heating system and is operated under a pressure of 450 mbars. The dichloropropane obtained after condensation in the condenser (210) is divided such that about 2.4 l per hour are introduced into the top of the column while about 1.375 g of dichloropropane per hour are removed via line (211). This 1,2-dichloropropane obtained via (211) is recycled to the production of the perpropionic acid solution. Product stream (211) contains about 0.2–0.3% by weight of water and traces of propionic acid. The head temperature of the column is about 80° C. A temperature between 125° and 130° C. is established in the bottom product.

The product mixture, freed from the solvent dichloropropane, is removed from the bottom of column (209) and passed via line (212) to column (213). This column (213) has a total of 30 actual trays in the form of bubble trays and a diameter of 50 mm. Stream (212), which contains 28%, by weight of ε-caprolactone, is introduced into column (213) at the 20th tray (counted from the bottom). The caprolactone is in turn removed as a vapor in a side stream at the level of the 10th tray. The column is operated under a pressure of 30 mbars and a reflux ratio of reflux (214) to take-off (215) of 1:1. Column (213) is likewise heated with a circulatory evaporator, downstream of which, however, a thin film evaporator is located. The high-boiling constituents, which essentially contain adipic acid, in addition to polymeric caprolactone, introduced into the column are discharged from the process via line (216) as the outflow of the thin film evaporator. The amount of high-boiling constituents is only about 15 g per hour. A temperature of 138°–142° C. is established in the bottom of the column and the overhead temperature is 60° C. The ε-caprolactone discharged from (213) as a side stream via (217) has a purity of 99.7–99.9% and is obtained in an amount of 385 g/hour.

A mixture of propionic acid and cyclohexanone is obtained as the top product of column (213) and is introduced into column (218) via line (215). The average composition of stream (215) is 65.45% by weight of propionic acid, 34.45% by weight of cyclohexanone and about 0.1% by weight of caprolactone.

Column (218) is equipped with 50 actual trays and is heated by a circulatory evaporator. The inlet (215) is at the 20th tray, counted from the bottom. Column (218) is operated at a head pressure of 130 mbars and at a head temperature of 85° C. The reflux ratio is adjusted to 6:1. The lateral take-off for the product stream (204) is at the level of the 5th tray.

About 470–475 ml per hour of propionic acid are removed from (218) as the distillate via line (219) and are recycled to the preparation of the solution of perpropionic acid. Only traces of cyclohexanone can be detected in this propionic acid. Very small amounts of high-boiling constituents are removed from the bottom of column (218) via (220 and are passed to column (213).

The selectivity for ε-caprolactone is 96.5% relative to the perpropionic acid employed in reaction system (201) and 95.2% relative to cyclohexanone consumed, that is to say fresh cyclohexanone (203) fed into (201).

It will be understood that the specification and examples are illustrative but not limitative of the present invention and that other embodiments within the spirit and scope of the invention will suggest themselves to those skilled in the art.

What is claimed is:

1. A process for the preparation of ε-caprolactone comprising:
   (a) reacting cyclohexanone with a solution of perpropionic acid in an organic solvent selected from the group consisting of an aromatic hydrocarbon consisting 6 to 10 carbon atoms, an aliphatic or cycloaliphatic hydrocarbon containing up to 12 carbon atoms and a chlorinated hydrocarbon containing 1 to 10 carbon atoms and 1 to 4 chlorine atoms at a molar ratio of cyclohexanone; perpropionic acid of about 1.1–5:1 at a temperature of about 10° to 80° C. to form a reaction mixture consisting essentially of ε-caprolactone, propionic acid and organic solvent,
   (b) distilling the reaction mixture from (a) in a first distillation unit to obtain a distillate comprising the organic solvent and a distillation residue,
   (c) introducing the distillation residue from (b) into a second distillation unit to obtain a distillate comprising propionic acid and unreacted cyclohexanone, removing from the second distillation unit, separately from one another and at a point below the point of introduction into the second distillation unit, ε-caprolactone and any high-boiling constituents, and,
   (d) distilling in a third distillation unit the distillate from (c) to obtain a distillate consisting essentially of propionic acid and a distillation residue comprising a mixture of propionic acid and cyclohexanone.

2. A process according to claim 1, wherein the mixture comprising cyclohexanone and propionic acid which is obtained in stage (d) is recycled to reaction stage (a).

3. A process according to claim 1, wherein the mixture of propionic acid and cyclohexanone obtained in stage (d) contains about 0.5–50% by weight of propionic acid.

4. A process according to claim 1, wherein the molar ratio of cyclohexanone to perpropionic acid in (a) is about 1.5–2.5:1.

5. A process according to claim 1, wherein the reaction in stage (a) of cyclohexanone with the organic solution of perpropionic acid to produce ε-caprolactone is carried out at a temperature of about 20°–60° C.

6. A process according to claim 1, wherein the reaction of stage (a) is effected in a cascade of 5 to 20 ideally mixed reactors.

7. A process according to claim 1, wherein the concentration of perpropionic acid in the organic solution of perpropionic acid used in stage (a) is from about 5 to 30% by weight.

8. A process according to claim 1, wherein the organic solution of perpropionic acid used for the reaction in stage (a) has a water content of less than about 0.5% by weight, a hydrogen peroxide content of less than about 0.25% by weight and a strong acid content of less than about 100 ppm.

9. A process according to claim 1, wherein the organic solvent for the perpropionic acid under normal pressure has a boiling point at least about 15° C. below that of propionic acid.

10. A process according to claim 9, wherein the organic solvent for the perpropionic acid is benzene, 1,2-dichloropropane, trichloroethylene, tetrachloroethylene, methylene chloride and 1,2-dichloroethane.

11. A process according to claim 1, wherein the organic solution of perpropionic acid comprises a solution obtained by extraction of a mixture containing perpropionic acid, water, an acid catalyst, propionic acid and hydrogen peroxide with the organic solvent.

12. A process according to claim 1, wherein the reaction mixture distilled in the first distillation unit of stage (b) comprises about 5–30% by weight of ε-caprolactone and about 5–20% by weight of cyclohexanone.

13. A process according to claim 1, wherein the organic solvent distillate in stage (b) has a propionic acid content of less than about 1% by weight and is recycled to the production of the organic solution of perpropionic acid.

14. A process according to claim 1, wherein the ε-caprolactone is removed from the second distillation unit in (c) about 1 to 15 theoretical plates above the bottom, and any higher-boiling constituents which may have been introduced into the second distillation unit are discharged from the second distillation unit as the bottom product.

15. A process according to claim 1, wherein the mixture of propionic acid and cyclohexanone is taken off in (d) from the third distillation unit about 1 to 3 theoretical plates above the bottom.

16. A process according to claim 1, wherein the propionic acid obtained as the distillate in (d) in the third distillation unit has a cyclohexanone content of less than about 0.5% by weight and is recycled to the production of the perpropionic acid.

17. A process according to claim 1, wherein the second distillation unit in (c) is operated under a pressure of about 5–500 mbars.

18. A process according to claim 1, wherein the higher-boiling constituents obtained as the bottom product in the third distillation unit of (d) are introduced into the second distillation unit of (c) at a point above the ε-caprolactone take-off.

19. A process according to claim 1, wherein the solvent is benzene.

20. A process according to claim 1, wherein the solvent is 1,2-dichloropropane.

* * * * *